United States Patent
Darlington et al.

(10) Patent No.: US 9,927,339 B2
(45) Date of Patent: Mar. 27, 2018

(54) DEVICE, SYSTEM AND METHOD FOR DYNAMIC TESTING OF GROUND SUPPORT BOLTS, ANCHOR BOLTS OR ROCK BOLTS

(71) Applicant: SANDVIK INTELLECTUAL PROPERTY AB, Sandviken (SE)

(72) Inventors: Bradley Darlington, Wellard (AU); Marten Bjorn Karlsson, Yangebup (AU); Mieczyslaw Rataj, New South Wales (AU)

(73) Assignee: SANDVIK INTELLECTUAL PROPERTY AB, Sandviken (SE)

( * ) Notice: Subject to any disclaimer, the term of this patent is extended or adjusted under 35 U.S.C. 154(b) by 102 days.

(21) Appl. No.: 14/765,725

(22) PCT Filed: Feb. 5, 2014

(86) PCT No.: PCT/IB2014/058793
§ 371 (c)(1),
(2) Date: Aug. 4, 2015

(87) PCT Pub. No.: WO2014/122583
PCT Pub. Date: Aug. 14, 2014

(65) Prior Publication Data
US 2016/0025608 A1    Jan. 28, 2016

(30) Foreign Application Priority Data
Feb. 5, 2013   (AU) ................................. 2013900365

(51) Int. Cl.
*G01N 3/303*     (2006.01)
*E21D 21/00*    (2006.01)
(Continued)

(52) U.S. Cl.
CPC ......... *G01N 3/303* (2013.01); *E21D 21/0093* (2013.01); *F16B 7/0426* (2013.01); *G01L 5/00* (2013.01); *G01M 7/08* (2013.01)

(58) Field of Classification Search
CPC ..... G01L 15/0033; E02D 33/00; B64D 17/38; B64D 17/383; Y10T 403/5741;
(Continued)

(56) References Cited

U.S. PATENT DOCUMENTS 5,846,015 A * 12/1998 Mononen ................ F16C 1/101
                                                                    118/119
2003/0068193 A1 * 4/2003 El-Haw .................. B60G 7/005
                                                                    403/56
(Continued)

FOREIGN PATENT DOCUMENTS

DE          2513670 A1    10/1976
DE    102009016505 A1 *  10/2010 .......... B60L 11/1825
DE    102010040519 A1     3/2012

OTHER PUBLICATIONS

Beverlymountainguide, Ice Screw Drop Test, YouTube video, https://www.youtube.com/watch?v=s8BEINmp048, May 2009.*
(Continued)

*Primary Examiner* — Daniel J Colilla
(74) *Attorney, Agent, or Firm* — Corinne R. Gorski (57) ABSTRACT

A connector, an associated dynamic testing system and method for testing rock bolts or rock anchors in situ. The connector is attached to a rock bolt/anchor and supports a hanging load via a shaft. The connector has a body of two halves retaining upper first and lower second connectors having respective curved surfaces. Each of the two halves has a curved inner surface allowing limited relative rotational movement of the first and second connectors relative to the two halves when a load is applied. A load cell and
(Continued)

accelerometer register the load applied to the rock bolt/anchor through the connector and any resulting movement of the rock bolt/anchor.

17 Claims, 11 Drawing Sheets

(51) Int. Cl.
  *G01M 7/08* (2006.01)
  *F16B 7/04* (2006.01)
  *G01L 5/00* (2006.01)

(58) Field of Classification Search
  CPC ........... Y10T 403/5761; Y10T 24/1451; E21D 21/0093; F16B 7/0426; G01N 3/303
  See application file for complete search history.

(56) References Cited

U.S. PATENT DOCUMENTS

| | | | | |
|---|---|---|---|---|
| 2004/0155219 A1* | 8/2004 | McCarty | ............... | F16B 7/0426 251/357 |
| 2012/0031320 A1* | 2/2012 | Bauduin | ............... | B63B 21/502 114/264 |
| 2013/0105247 A1* | 5/2013 | Casebolt | .................. | A62B 1/10 182/241 |

OTHER PUBLICATIONS

Carlton et al., In situ dynamic drop testing of the MD bolt at Mt Charlotte Gold Mine; Ground Support 2013, pp. 217-220, Australian Centre for Geomechanics, Perth, 2013.*

Li et al., Dynamic tests of a new type of energy absorbing rock bolt—the D bolt, Paper 4136, Proceedings of the $3^{rd}$ CANUS Rock Mechanics Symposium, Toronto, May 2009.*

Salim et al., Shock Load Capacity of Concrete Expansion Anchoring Systems in Uncracked Concrete, Journal of Structural Engineering, pp. 1206-1215, Aug. 2005.*

* cited by examiner

DEVICE, SYSTEM AND METHOD FOR DYNAMIC TESTING OF GROUND SUPPORT BOLTS, ANCHOR BOLTS OR ROCK BOLTS

RELATED APPLICATION DATA

This application is a § 371 National Stage Application of PCT International Application No. PCT/IB2014/058793 filed Feb. 5, 2014 claiming priority of AU Application No. 2013900365, filed Feb. 5, 2013.

FIELD OF THE INVENTION

The present invention relates to dynamic testing of ground support bolts such as anchor/rock bolts.

BACKGROUND TO THE INVENTION

Rock bolts are long anchor bolts used to stabilise excavations in rock, such as tunnels and rock faces. A rock bolt transfers load at the exterior surface of the rock into the interior mass of the rock. Anchor bolts are used to securely attach objects to rock or concrete surfaces.

The 1890s first saw the use of rock bolts. The St Joseph Lead Mine in the USA in the 1920s is recorded as having used rock bolts.

Australia and the USA have both been recorded as using rock bolts in civil applications in the late 1940s. In 1947 Australian engineers were reported as experimenting with four meter long expanding anchor rock bolts during work on the Snowy Mountain scheme.

Rock bolts are typically installed in a pattern, the actual arrangement depending on the type of rock (rock quality—position and type of fractures already present, strength of the rock and its propensity to fracture etc.), the type of excavation (tunnel, cut face etc.) and the surrounding geology/geography (risk of seismic activity and any nearby underground or overground workings/structures).

Both rock bolts and anchor bolts can be used to retain a metal (wire) mesh over a rock face to reduce risk of loose material or rock fall that might injure personnel, damage vehicles/equipment and/or block a tunnel.

As with anchor bolts, there are many types of proprietary rock bolt designs. Typically a mechanical means, epoxy means or combination of both is used to set the bolt into the rock/concrete.

Rock bolts work by 'knitting' the rock mass together sufficiently before it can move enough to loosen and fail. Rock bolts can become 'seized' throughout their length by small shears in the rock mass, so they are not fully dependent on their pull-out strength.

In the case of a rock bolt, it is important to ensure that the rock bolt is capable of retaining the rock in situ when installed. In the case of an anchor bolt, it is important to ensure the item secured by the bolt is safely retained.

Static testing is an alternative form of test. This can be carried out in a laboratory or in situ. A continuous load is applied to the rock bolt, usually hydraulically. However, static testing does not simulate the 'shock' loading to the bolt present in dynamic testing.

Dynamic tests are conducted to ensure the respective bolt can operate as required. For rock bolts, a dynamic test is carried out in laboratory using a simulated bore-hole whereby the rock bolt is secured in a cement/resin mix inserted into a hollow (steel) tube. The tube is supported as a load acts on the head of the rock bot. This involves hydraulically applying a pull out force to the rock bolt.

Whilst laboratory simulation is useful, it does not accurately recreate working conditions and cannot perform an in-situ dynamic test on a bolt for the actual rock. Laboratory dynamic testing involves setting the rock bolt in the tube and suspending the tube and rock bolt from a raised support. A weight is dropped a preset distance to apply a shock load to the head of the bolt. The amount of weight and distance dropped determines the amount of force applied to the rock bolt.

Another form of laboratory testing involves dropping the rock bolt and tube combination together with a weight attached to the rock bolt. Fall of the rock bolt and tube is arrested once the required velocity is reached, but the weight is allowed to continue and thereby applies a load to the rock bolt. This method is said to better simulate the movement of the rock before the rock face fails (i.e. during a seismic event). Such testing is carried out by the Western Australian School of Mines (WASM) and is known as the WASM momentum transfer concept.

With the aforementioned in mind, the resent invention has been developed in order to provide improved in situ dynamic testing for rock bolts (and optionally anchor bolts).

SUMMARY OF THE INVENTION

The present invention provides in one aspect a connector to attach a loading device to an in situ ground support bolt, such as a rock bolt or anchor bolt in a rock or concrete substrate, the connector including a body, a first attachment means to attach the body to an in situ rock bolt or anchor bolt, and a loading device connection.

The loading device connection may include a second attachment means to releasably attach the loading device to the body.

The body may be unitary or may include multiple portions. For example, the body may be divided into portions that are releasably connectable together by one or more integral or detachable fastening means.

The connector may include at least one first curved surface on a cavity within the body, and a corresponding second curved face associated with the first attachment means. The first and second curved faces permit relative movement of the first attachment means and the body.

The connector may include a third curved surface, which may be within the first cavity or may be within a second cavity of the body. A fourth curved surface may contact the third curved surface to allow relative movement of the loading device and the body.

The cooperating first and second curved surfaces may be complimentary part spherical surfaces, such that movement of one surface relative to the other is multi directional. Likewise, the cooperating third and fourth surfaces may be part spherical surfaces, such that movement of the third surface relative to the fourth surface is multi dimensional. The part spherical surfaces allow for the rock bolt not being vertical in situ. Often rock bolts are angled from vertical into the rock. Relative movement of the first attachment means to the body, and the body to the loading device, allows the connector to transfer impact forces from a vertically dropped weight into the non-vertical rock bolt.

The first attachment means may include rock bolt connection means to attach the connector to the rock bolt. The rock bolt connection means may include an aperture to receive a shaft portion of the rock bolt. A nut on the external exposed end of the rock bolt may be used to retain the first attachment means to the rock bolt. Preferably the attachment via the nut of the rock bolt transfers the test load forces to the rock bolt.

Preferably the body has two or more portions arranged to be releasably held together by one or more fasteners. Release of the one or more fasteners allows the body to separate such that at least one of said portions can be removed.

The body may include two halves that are held together, in use, by the one or more fasteners. The one or more fasteners may include screw thread fasteners (such as bolts) directly into/through the body portions. Alternatively, or in addition, one or more retaining plates may be used. A said retaining plate may include a metal ring with holes therethrough to receive bolts. Bolts may be passed through aligned holes on each ring and nuts attached to the bolts to retain the two halves tightly together once the nuts and bolts are tightened.

The portions of the body may include flanges or lips, each flange or lip acting as a stop for one of the plates. Thus, when the bolts and nuts are tightened, the rings apply forces to the flanges/lips to hold the two halves together.

One or more forms of the present invention includes means to prevent damage to an electrical connector of a load cell provided within the connector. Such protection may include at least one metal projection adjacent the electrical connector. For example, a pin or bolt projecting above the load cell electrical connector and a tab of a washer projecting below the load cell electrical connector.

A further aspect of the present invention provides a dynamic testing system for testing rock bolts and anchor bolts in situ, the system including a loading device and a connector to releasably attach the loading device to an in situ rock bolt or anchor bolt, the loading device including at least one releasable weight to apply an impact load through the connector to the rock bolt or anchor bolt when released, and a weight release device, the connector including at least two portions releasably connectable together.

The system may include the abovementioned connector and features thereof.

A method of testing a rock bolt or anchor bolt in situ, the method including connecting a connector to an exposed portion of the rock or anchor bolt, attaching a weight drop assembly to the connector, providing a weight release mechanism to remotely release the weights during testing, the connector including at least one curved surface allowing the weight drop assembly to hang at or near vertical if the rock bolt or anchor bolt in situ is not vertical.

One or more forms of the present invention advantageously provides for in-situ dynamic testing of ground support members (such as rock bolts) with the ability to record load and displacement of the ground support member (e.g. rock bolt). There are no assumptions required with the rig or the testing, as the rock bolts are already installed in site rock and loaded under test as required.

Some features and benefits of the system include:

The test system (Dynamic Testing Rig) can be readily transported to any mine site. No requirement for testing to be restricted to an offsite test facility.

The test system (rig) is fully self contained (preferably only requires access to mine supply air to run the lifting hoist, though bottled compressed air/nitrogen can be brought in).

Requires only one person, such as an IT (Integrated tool-handler), to assemble and disassemble the test system.

Static test on bolt prior to dynamic test (optional if required).

Energy application levels are readily adjustable. For example, in increments of 8.2 kJ (with optional minor 'fine tuning' adjustments of 1.8 kJ).

Can be used to test any dynamic bolt in-situ. Custom dynamic collars (connector halves) may be provided.

Repeated loading on single bolts possible.

Allows free displacement until drop rig impacts with floor (not typically experienced).

BRIEF DESCRIPTION OF THE DRAWINGS

Embodiments of the present invention will hereinafter be described with reference to the accompanying drawings, in which.

DESCRIPTION OF PREFERRED EMBODIMENT

Figure 1:
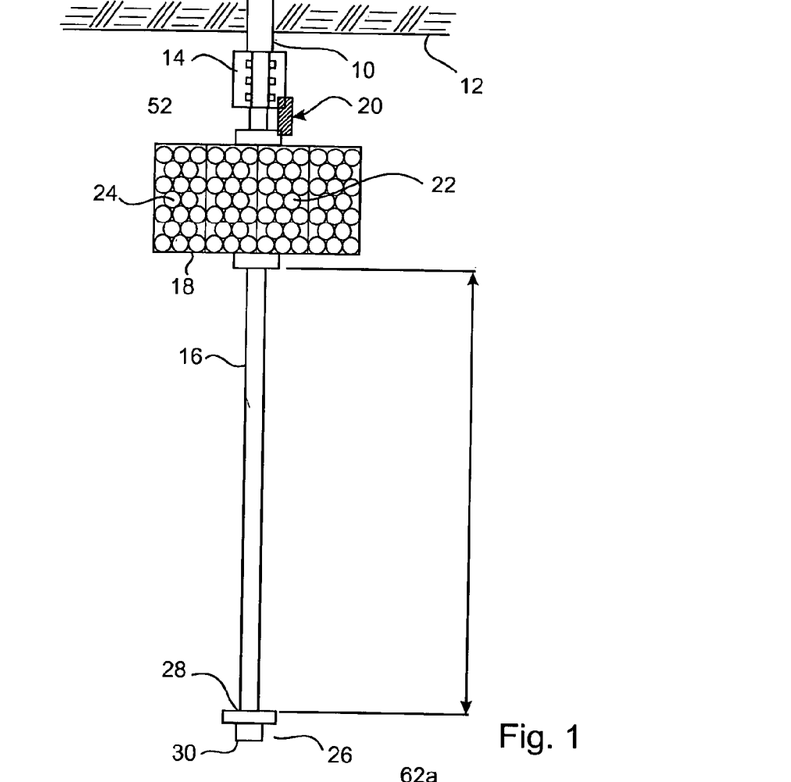
FIGS. 1 to 3 show an example of a connector and test system utilising the connector according to an embodiment of the present invention.
Figure 2:
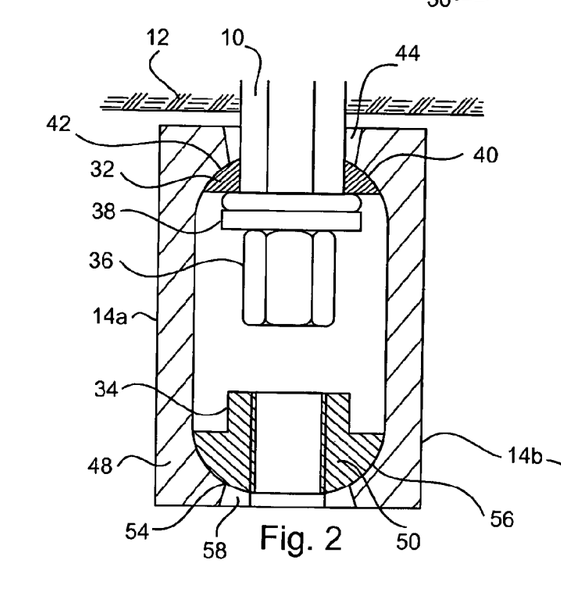
Figure 3:
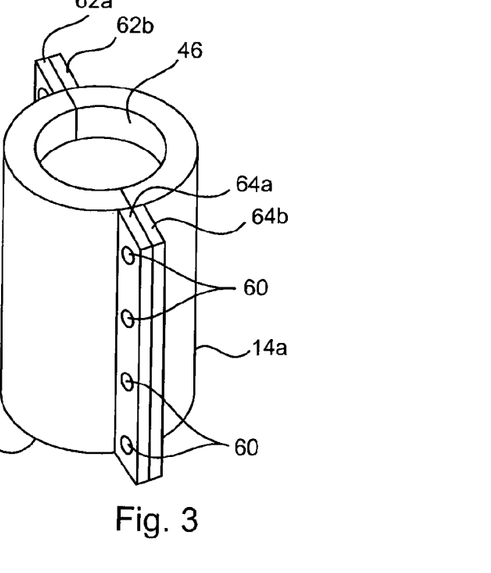

FIGS. 1 to 3 show an embodiment of a dynamic test system for rock bolts. It will be appreciated that the same system can be used to test anchor bolts in rock and concrete by selecting the amount of weight and drop height for the type of anchor bolt (or rock bolt) for a given application.

As shown in FIG. 1, a rock bolt 10 is set vertically in an overhead mass of rock 12 (such as a roof of a tunnel). A connector 14 connects the head end of the rock bolt to a shaft 16. A weight 18 is mounted for movement along the shaft when released by a quick release mechanism 20. The weight comprises a container 22 to hold multiple individual weights 24. The amount of individual weights in the container controls the total weight of the container and weights for a required test.

It will be appreciated that alternative weights can be used. For example, flat plate weights slotted onto the shaft rather than loose weights in a container. A stop member 26 prevents the container/weights coming off the end 30 of the shaft. A threaded nut may be provided to act as or retain the stop member.

The connector 14 is vertically divided into two halves 14a, 14b. (see FIGS. 2 and 3 for detail). Which clasp around the head end of the rock bolt and the upper end of the shaft.

As shown in FIG. 2, a first attachment means 32 retains the nut 36 and washer 38 at the head end of the rock bolt. The first attachment means has a curved surface 40 that contacts a corresponding curved surface 42 formed on the inside faces of the two halves of the connector. The mutually curved contact surfaces 40, 42 allow the connector several angular degrees of movement about the rock bolt head. This positional ability accommodates the test system acting on a non-vertical rock bolt. A tapered opening 44 with tapered surface on the connector allows for the movement of the connector relative to the shaft/head of the rock bolt and acts as a stop limit.

The lower end of the connector 48 accommodates a second attachment means 50 that has an aperture therethrough to receive the upper end of the shaft (not shown in FIG. 2). A nut retains the upper end of the shaft in a similar way to the head of the rock bolt against the first attachment means. The second attachment means can attach by screw thread onto the upper end of the shaft.

The second attachment means includes a curved surface 54 and the two halves of the connector form a mutually curved interior surface 56 that contacts the curved surface of the second attachment means to allow angular degrees of freedom of movement of the second attachment means, and therefore the shaft and weights, relative to the connector (and therefore relative to the rock bolt). This arrangement allows the test rig to act on the in situ rock bolt even if the rock bolt is not vertical.

The connector 14 shown in FIGS. 1 to 3 has multiple holes 60 through paired flanges 62a, 62b and 64a, 64b. Bolts through the holes in the flanges are used to hold the two halves together in situ.

Figure 4:
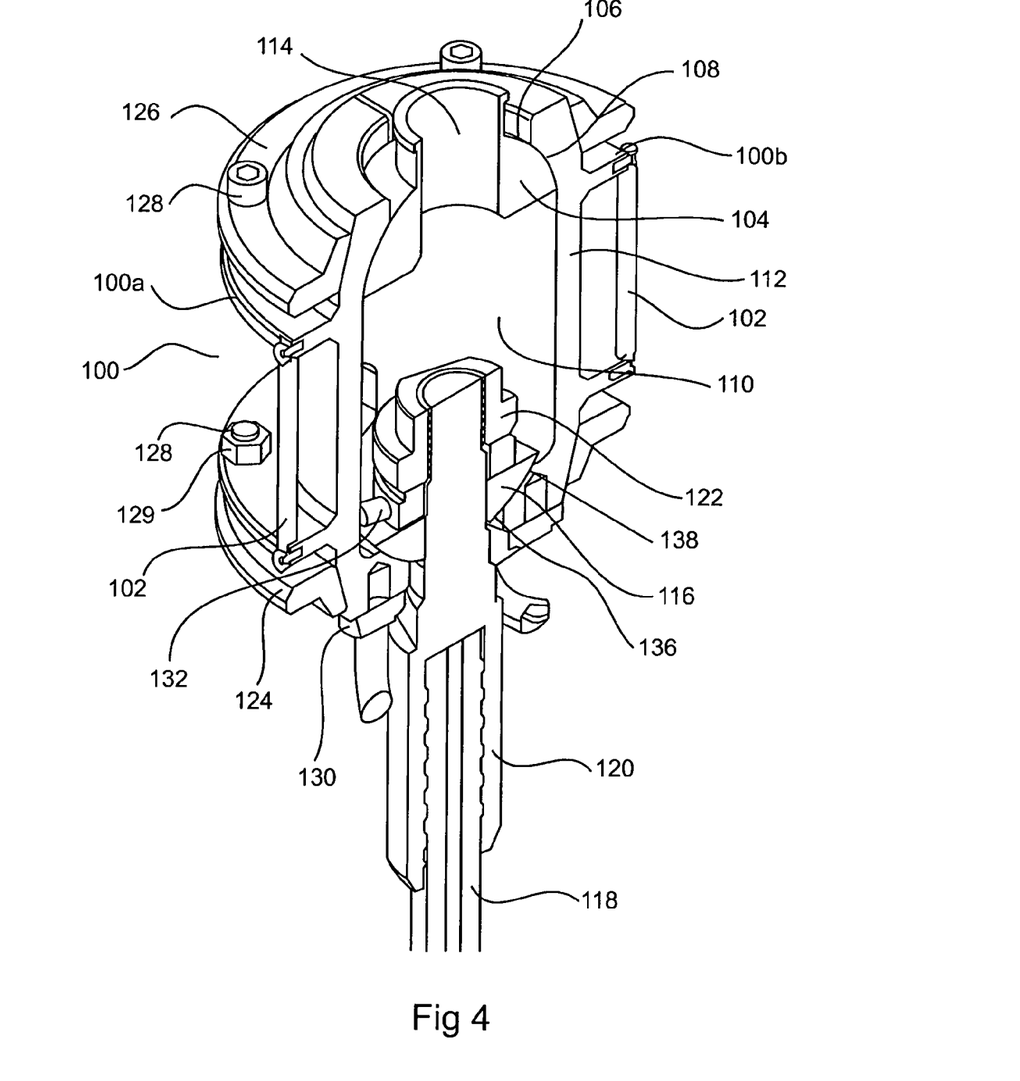
FIG. 4 shows a cross section in perspective of an alternative embodiment of the connector.

The alternative embodiment of a connector 100 of the present invention shown in FIG. 4 operates in a similar manner to the connector shown in FIGS. 1 to 3. The connector 100 includes two vertically separated portions 100a, 100b. Each portion includes at least one handle 102 to assist with lifting and holding each portion when mounting to the rock bolt.

It will be appreciated that the head nut of the rock bolt may or may not be loosened or removed so that the first attachment means can be mounted to the head of the rock bolt after installation of the rock bolt. Alternatively, during installation of the rock bolt, the first attachment means or an adapter or spacer for connection of the connector can be attached to the rock bolt so that the head nut of the rock bolt is not removed to connect the connector.

The end of the rock bolt exposed out of the rock passes through the aperture 114 in the first attachment means. The two halves 100a, 100b of the connector 100 are then placed about the first attachment means with the second attachment means 116 suspending the shaft 118 via a shaft adapter 120 and nut 122.

Figure 7:
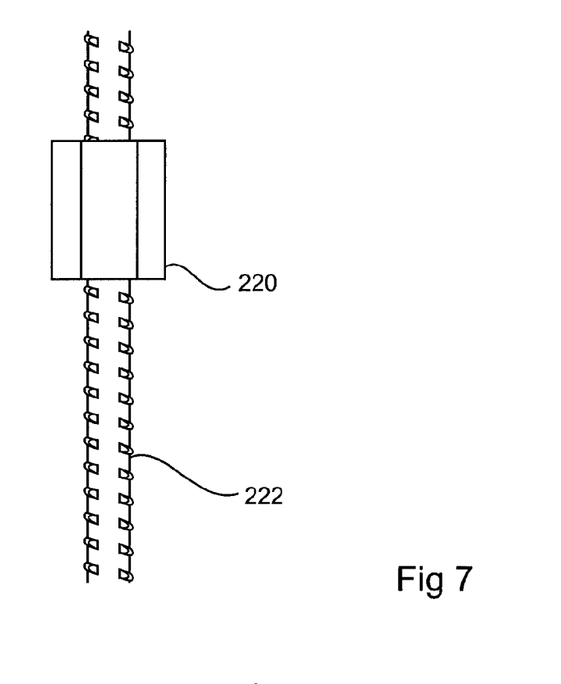
FIG. 7 shows a nut threaded onto an exposed end of a rebar ground support bolt to apply an adapter or the first attachment means to the bolt to then receive the connector according to an embodiment of the present invention.

Alternatively, an adapter or the first attachment means can be retain on an exposed end of a ground support bolt (such as a rock bolt) by a nut threaded onto the shaft of the bolt. As shown in FIG. 7, a nut 220 can be threaded onto a shaft 222 of the bolt.

The shaft of the bolt can be rebar (reinforcing bar) with a discontinuous external thread formed on its external surface). The nut can be or include a spacer or adapter to retain the connector body, or can retain an adapter or spacer in place.

Figure 8:
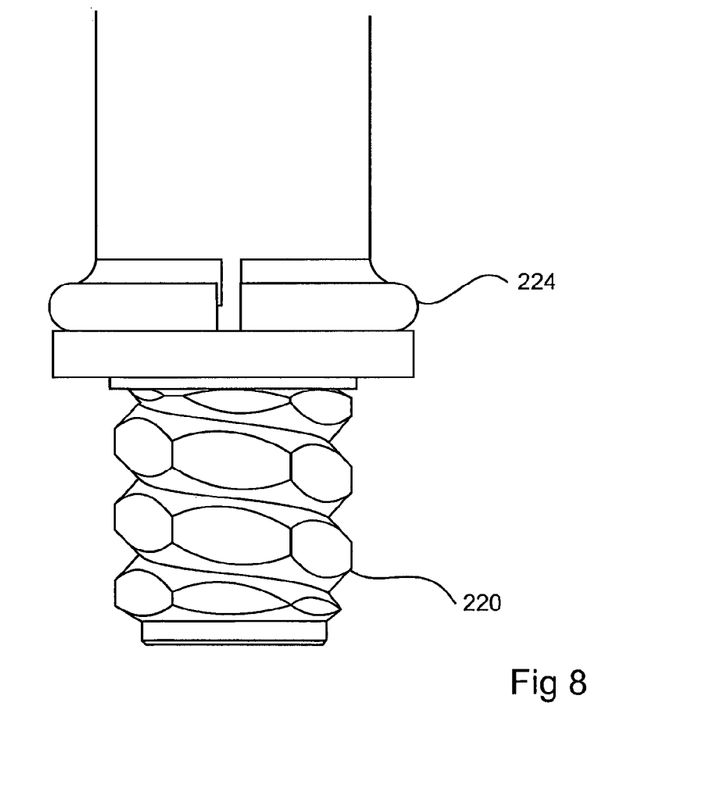
FIG. 8 shows an adapter threaded onto an external thread on a nut of a ground support bolt (such as a rock bolt) to retain a connector on the bolt according to an embodiment of the present invention.

As shown in FIG. 8, the nut on the ground support bolt (rock bolt) can be externally threaded to threadingly receive a spacer or adapter 224 thereon. Thus, the connector can be supported directly on the nut of the ground support bolt.

Alternatively, the nut of the ground support bolt can be removed and replaced by a spacer/adapter to retain the connector or a spacer/adapter can be added to be retained by the nut.

Lower 124 and upper 126 rings bolt the two portions 100a, 100b together. The bolts 128 can pass through both rings or separate bolts 129 can be used for each ring.

The connector can be provided with load and/or acceleration sensing devices. For example, an accelerometer 130 can be provided to detect downward movement/acceleration of the connector (and therefore of the connected rock bolt).

The accelerometer 130 is electrically connected (hard wired or wireless) to communicate with a data receiving means, such as a computer, processor or memory device for later processing of data.

A load cell 132 can be provided to detect load forces resulting from the impact of the weight(s) and therefore detecting the load applied to the rock bolt. The load cell is applied to a washer or spacer or is formed as a ring between the nut 122 retaining the shaft and the second attachment means 116. Thus, acceleration data and load data can be gathered and analysed to determined load forces applied to the rock bolt and detect any movement of the rock bolt resulting from the test.

As with the first attachment means, the second attachment means 116 includes a curved surface 136 arranged to contact a complimentary curved surface 138 on the inside of the cavity formed by the two body portions of the connector.

The first attachment means 104 has a curved surface 106 that contacts a complimentary curved surface 108 on the inside of the cavity 110 of the connector. The curvature of each surface is preferably part spherical to allow angular degree of freedom for the connector body 112 (comprising the two connected portions) about the head of the rock bolt.

Figures 5, 6:
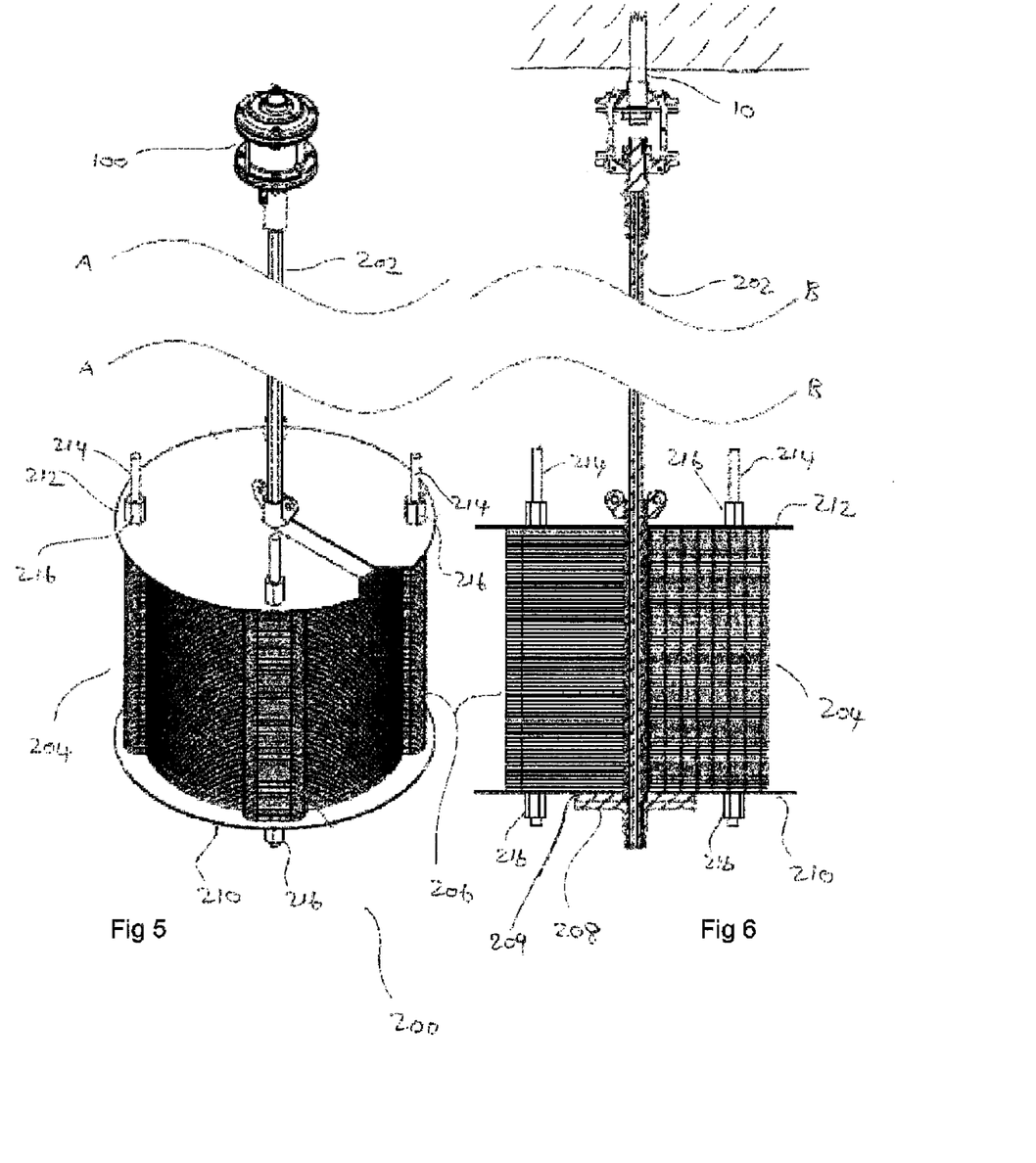
FIGS. 5 and 6 show perspective (FIG. 5) and side sectional view (FIG. 6) of a test system according to an embodiment of the present invention.

The test system 200 includes a connector 100 (as shown in FIG. 4) from which is suspended a shaft 202 and assembly of weights 204. FIG. 6 is a cross sectional view, and shows the connector 100 connected to a rock bolt 10.

The weights 206 are plates stacked one on top of another to achieve the desired downward force and to apply a required shock force to the rock bolt through the assembly when the weights are dropped and then arrested by the weight stop 208 attached to the lower end of the shaft.

The weights are supported on a lower plate 210 and safely retained in place by an upper retainer plate 212 by through bolts 214 and retainer nuts 216. The wavy horizontal lines A,B in FIGS. 5 and 6 indicate that the shaft can be of any desired length.

In use, the connector is connected to an adapter or to the first attachment means attached to the rock bolt head. The shaft and weights are suspended from the connector. The desired amount of weight is set for release by a release mechanism to allow the weights to drop down the shaft. The shock of the arrested weights is measured as a sudden pull force on the rock bolt, and any movement of the rock bolt and the amount of force applied can be measured respectively by the accelerometer and load cell in the connector. Such dynamic testing on rock bolts or anchor bolts in situ enables the performance of the rock bolt or anchor bolt to be assessed under site specific conditions.

Benefits of the dynamic test system are that it can apply 25 kJ of energy to the bolt, can detect slip/deformation of the bolt arising from energy application, allows remote release of the weight a a safe distance from the test area, is readily assembled for use and disassembled on site, and can be installed and operated by one or two personnel.

Figure 9:
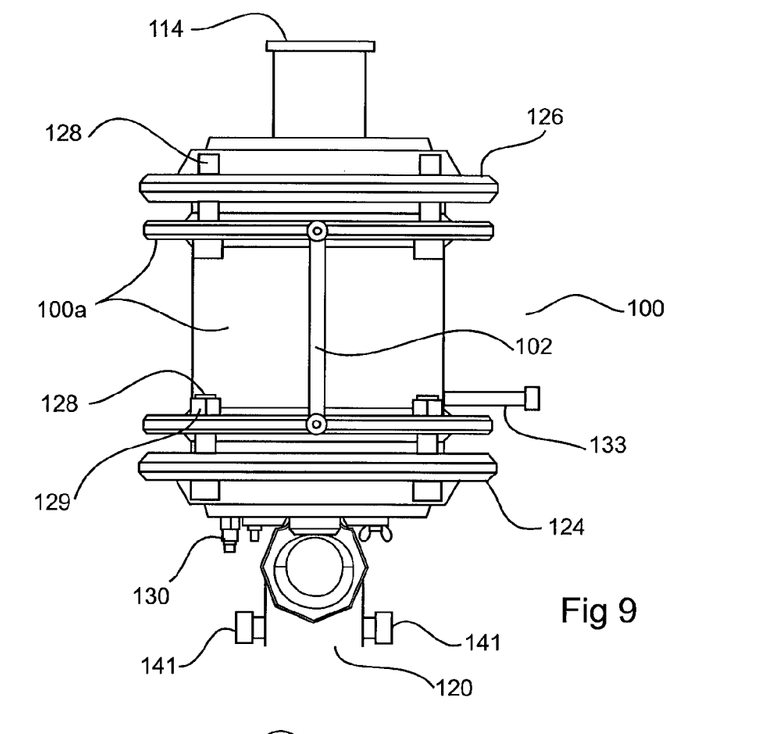
FIGS. 9 and 10 show side on external views of the connector forming part of a dynamic testing rig/assembly according to an embodiment of the present invention.
Figure 10:
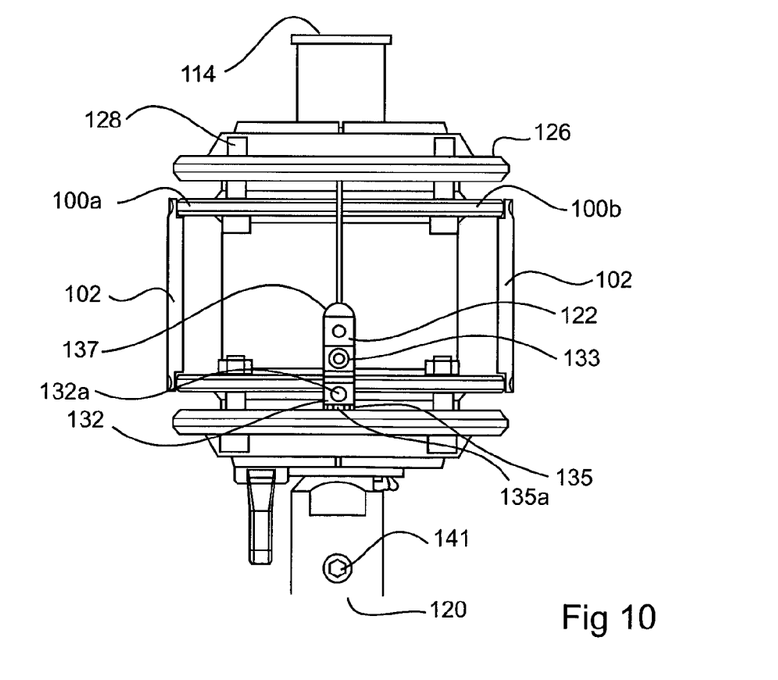

FIGS. 9 and 10 show respective side views of the connector of a dynamic testing system according to an alternative embodiment of the present invention. Reference numbering is the same as for the embodiment shown and described with reference to FIG. 4.

However, the embodiment shown in FIGS. 9 and 10 further includes a bolt 133 projecting through a gap 137 provided between the two halves 100a, 100b of the connector when assembled. The bolt, is mounted into the retaining nut 122 immediately above the load cell 132, and, in conjunction with an additional washer 135 (with its tab 135a) below the load cell, helps to protect the load cell 132 and its electrical connector 132a from impact damage. It was realised during trials of the dynamic testing system that the load cell and/or its electrical connector could become damaged in situations where the connector was initially not vertical when connected to the rock bolt and the load dropped, causing the connector to articulate via the complimentary curved surfaces 106, 108 and 136, 138 whereby the electrical connector of the load cell could suffer impact. The bolt and washer protect the load cell, and particularly the load cell electrical connector, during such relative movements of the two halves 100a, 100b and the first and second attachment means 104,116.

The shaft adaptor 120 also includes a releasable locking fastener 141 (e.g. a locking bolt or screw) to help retain the shaft 118 to the adaptor.

Figure 11:
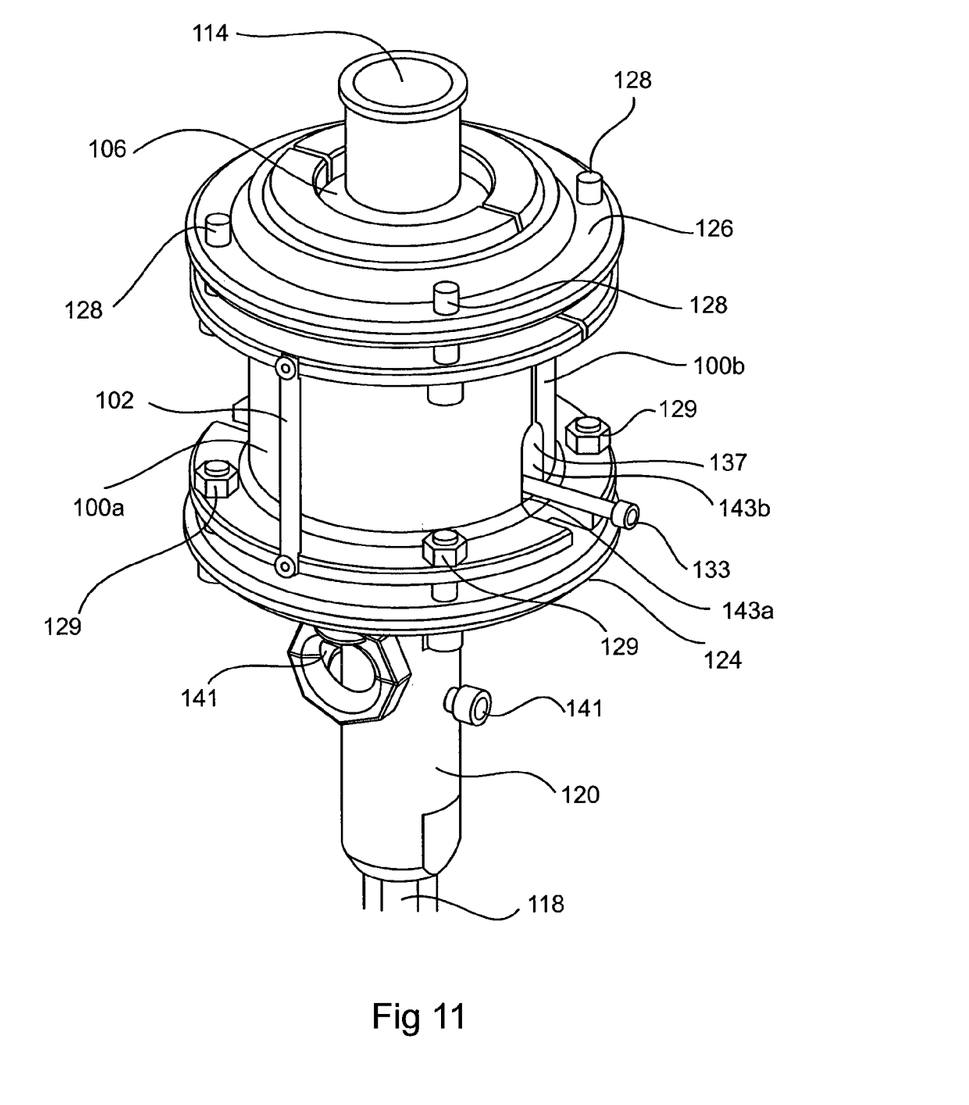
FIG. 11 shows in perspective view the connector of FIGS. 9 and 10.

FIG. 11 shows a perspective view of the connector shown in FIGS. 9 and 10.

Figure 12:
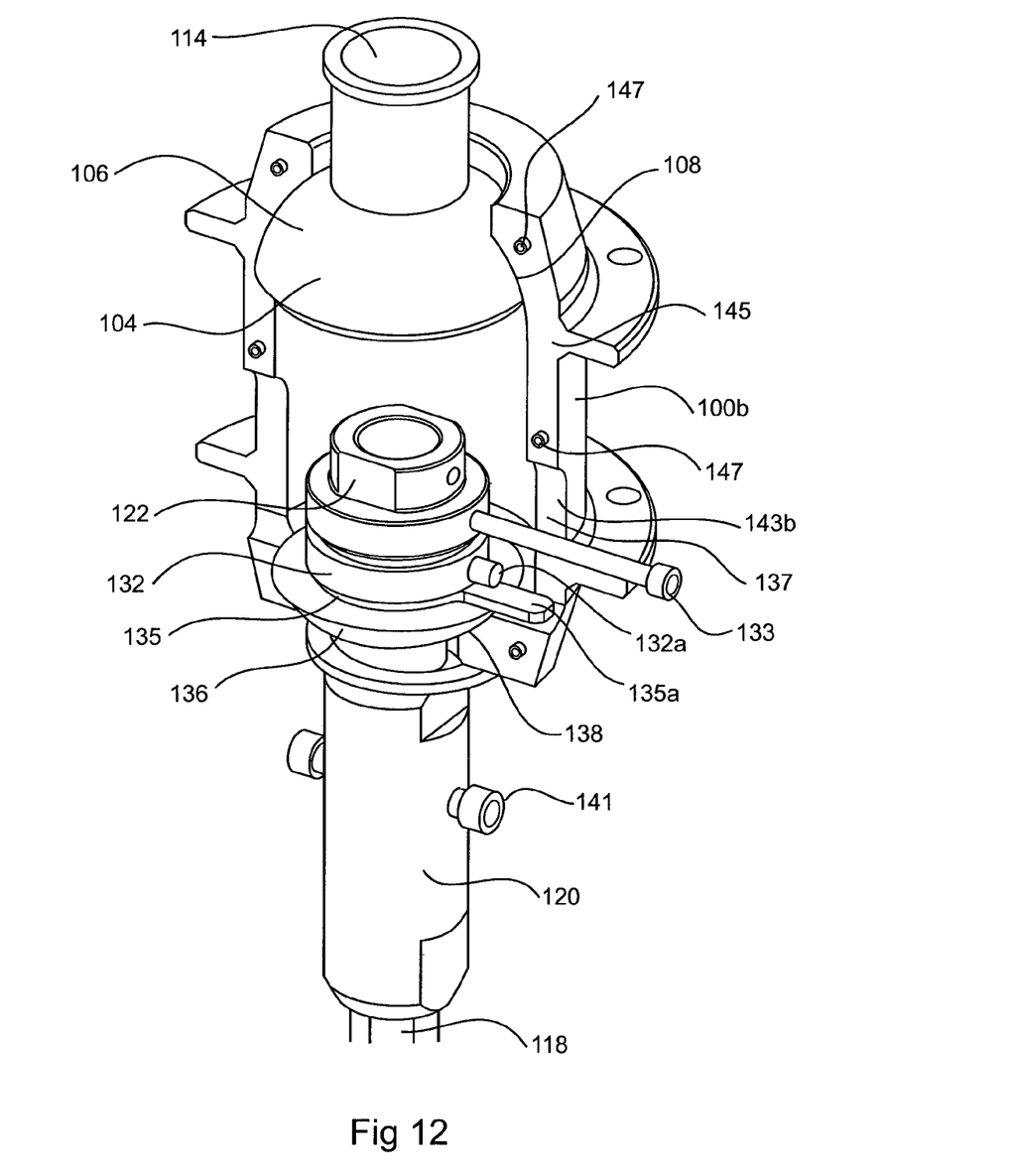
FIG. 12 shows a cutaway view of the connector of FIGS. 9-11 and showing the internal arrangement of components.

FIG. 12 shows a cutaway view of the connector 100 according to the embodiment discussed above in relation to FIGS. 9 to 11. The cutaway view shows the nearest connector half 100a removed and the second connector half 100b remaining in position.

The bolt 133 is shown projecting though the opening 137 formed by the cut-outs 143a, 143b in the respective connector halves 100a, 100b. The washer 135 is shown with washer tab 135a projecting into the opening 137. Thus, the load cell 132 and particularly its electrical connector 132a are protected from impact damage from above by the bolt 133 and from below by the washer and its tab 132a.

The mating face 145 of the connector half 102b shown includes locating projections 147 which match with corresponding recesses in the respective mating face of the other half 100a for correct positioning when connecting the two halves together.

Figure 13:
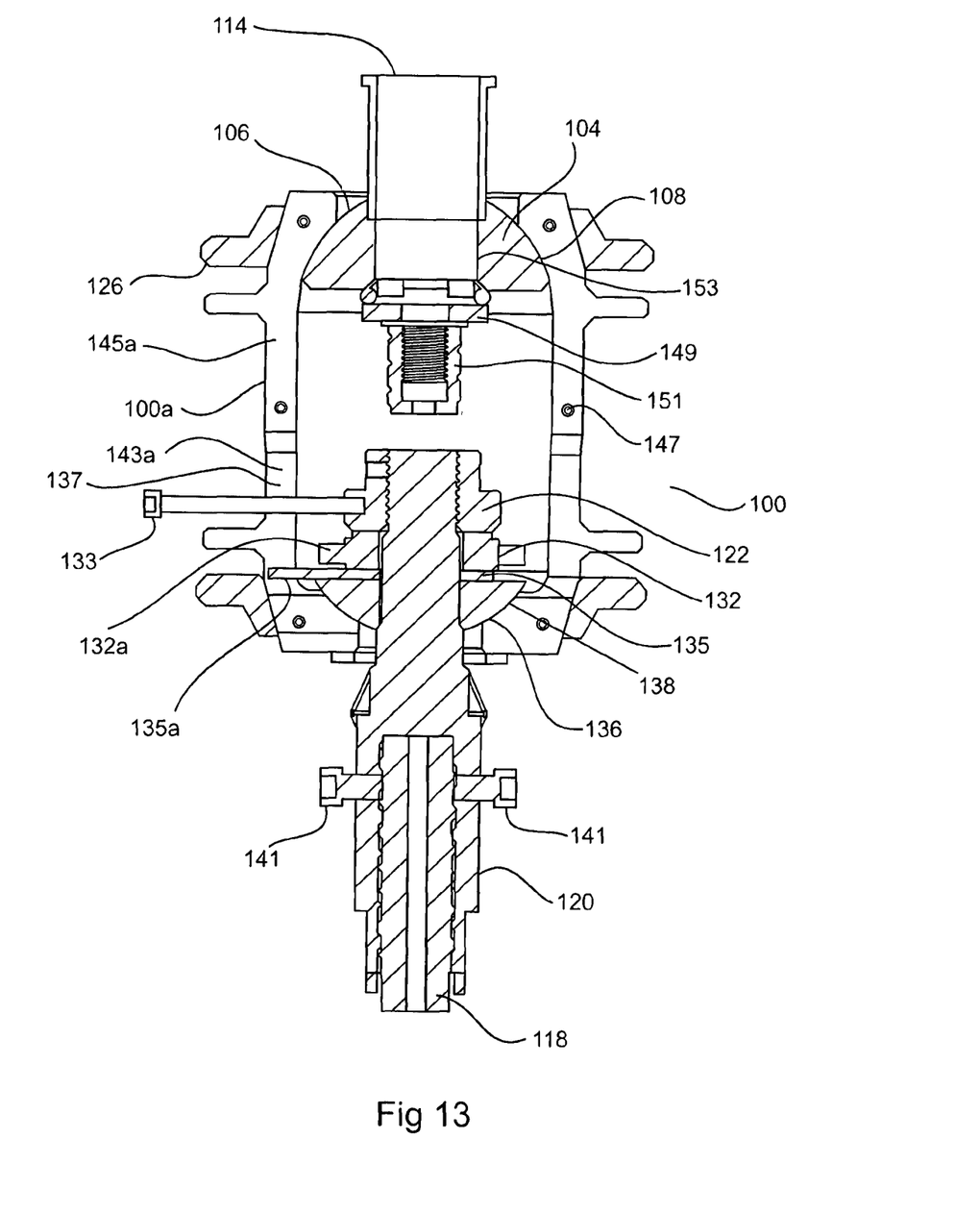
FIG. 13 shows a sectional view through the embodiment shown in FIGS. 9 to 12.

FIG. 13 shows a sectional view through the connector 100. This view clearly shows the internal arrangement of components within the connector of the dynamic testing system. The first connector 104 releasably attaches to the rock bolt/anchor via a nut 149 and shaft 151 of the pre-installed rock bolt/anchor.

Figure 14A:
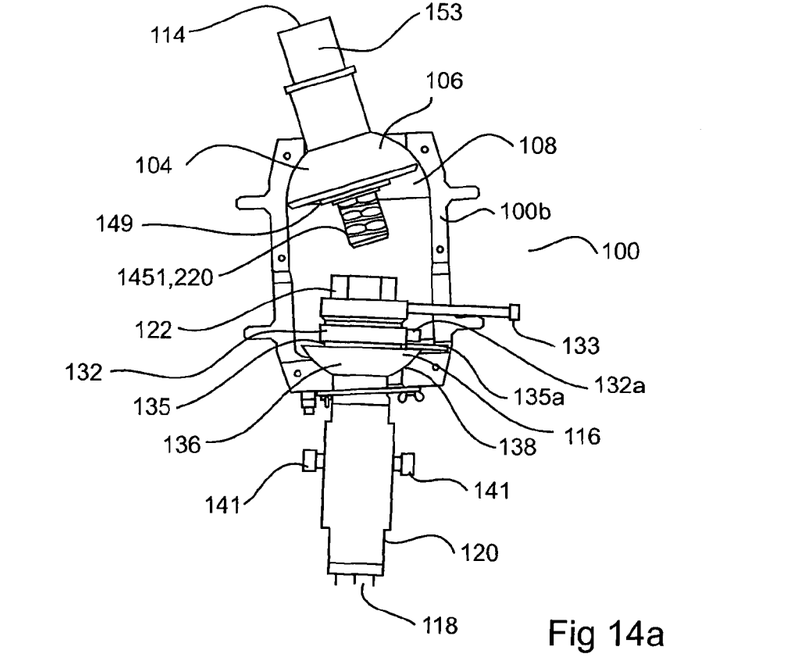
FIGS. 14a and 14b show respective side partial cutaway (FIG. 14a) and perspective partial cutaway (FIG. 14b) of an upper portion of the dynamic testing system including the connector and as attached to a non-vertical ground support bolt in-situ in a mine roof.
Figure 14B:
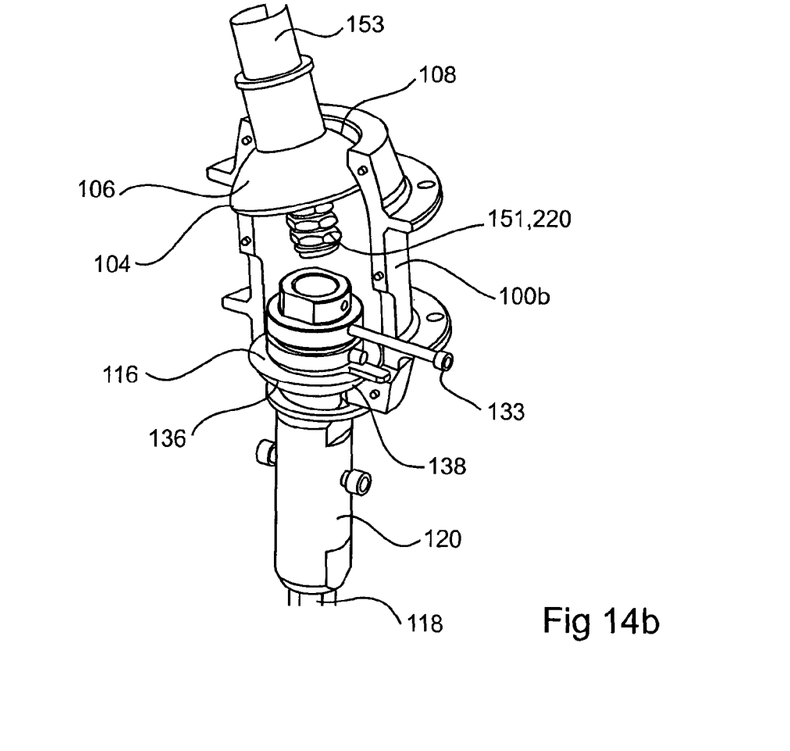

FIGS. 14a and 14b show how the connector 100 allows the supported shaft 118, 202 and weights assembly to be supported vertically from a non-vertical ground support bolt 153. The cooperating curved surfaces 108, 138 on the inside of the connector halves 100a, 100b allow the upper first connector portion 104 and lower second connector portion 116 to rotate relative to one another and relative to the two halves 100a, 100b. Thus, testing of non-vertically installed ground support bolts can carried out in-situ. This helps to ensure that load forces applied through impact of the weights when dropped are transferred through the shaft 118, through the connector to the ground support bolt as effectively as possible, and such articulation provided by the connector allows more ground support bolts to be tested in situ even if they are non-vertical and thus not ideally positioned. This helps to increase the overall number of ground support bolts tested and thereby improves mine safety.

Figure 15:
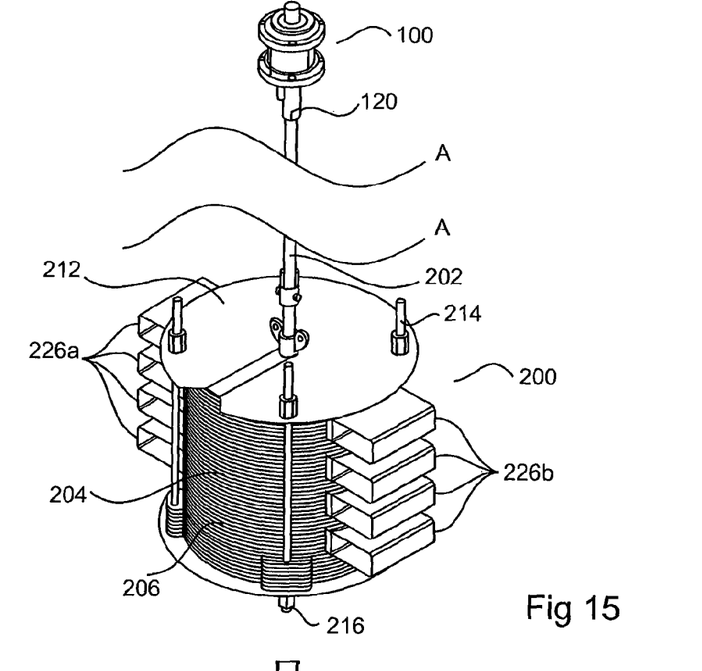
FIGS. 15 and 16 show perspective and side sectional views of the dynamic testing assembly/rig with suspended weights according to an embodiment of the present invention.
Figure 16:
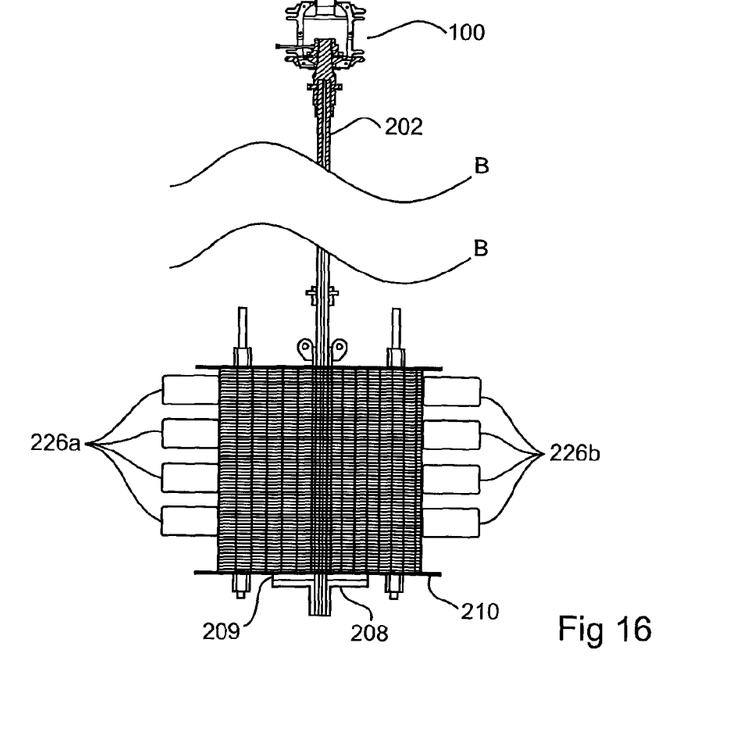

FIGS. 15 and 16 show respective perspective and side sectional views of the dynamic testing system 200 of an embodiment of the present invention. The connector 100 previously described above connects overhead to a rock bolt (not shown) in situ in a mine roof, as in FIG. 6.

The system as shown in FIGS. 15 and 16 is similar to that system shown and described in relation to FIGS. 5 and 6. However, the weights 206 are provided in set stacks, each stack comprising a number of weights, and each stack including fork lift lift/lower points 226a, 226b allowing groups of weights to be added or removed from the load 204 by a fork lift truck rather than manually moving one weight plate at a time by one or two people.

Operation of the testing system with the connector has been conducted in-situ at two mine sites.

Figure 17:
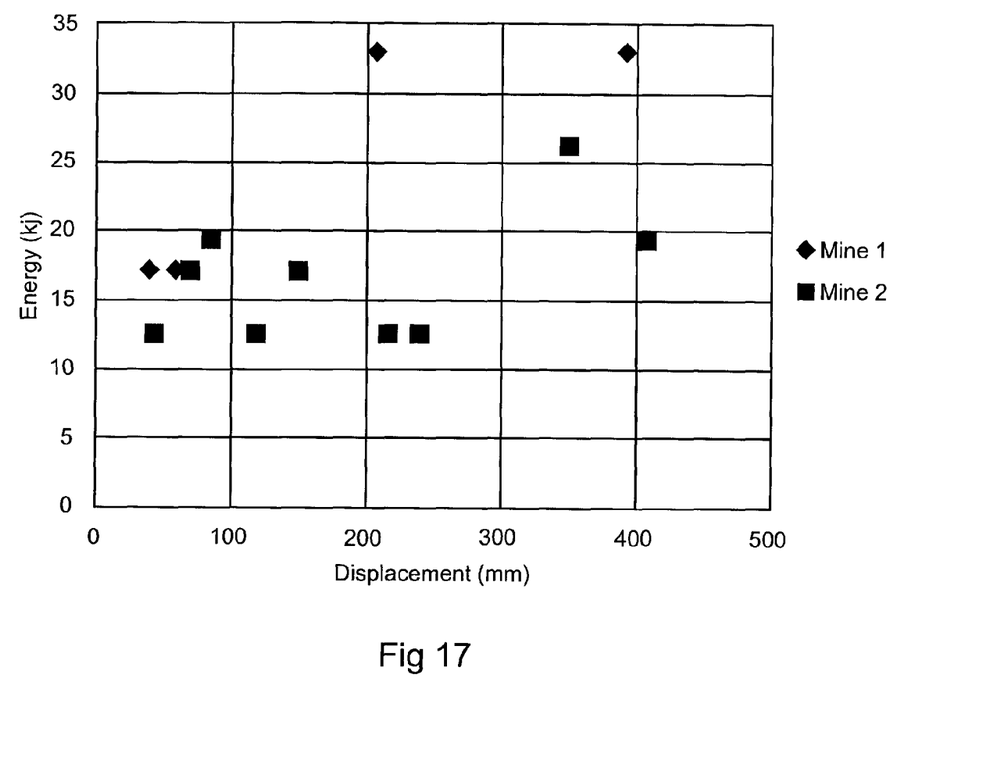
FIG. 17 shows a chart of energy displacement performance from in-situ tests conducted at two mine sites.

A pictorial summary of test data achieved from the two mine site tests is shown FIG. 17, which shows the data from Table 1 below.

Rock characteristics from the first mine site test (mine site 1) were UCS (Uniaxial Compressive Strength) of 200-310 MPa and a Q factor (Barton et al 1993) of 25-50.

For the second mine site test (mine site 2), the rock characteristics were a UCS of around 156 MPa and a Q factor of 2.5.

TABLE 1

| Mine site | Bolt No. | drop | energy (kJ) | slip (mm) |
|---|---|---|---|---|
| Mine 1 | 1 | 1 | 17.23 | 40 |
|  | 1 | 2 | 17.23 | 60 |
|  | 2 | 1 | 33.13 | 207 |
|  | 3 | 1 | 33.13 | 393 |
|  | 4 | 1 | 33.13 | — |
|  | 6 | 1 | 33.13 | — |
| Mine 2 | 1 | 1 | 17.1 | 150 |
|  | 1 | 2 | 17.1 | 69 |
|  | 2 | 1 | 19.4 | 407 |
|  | 2 | 2 | 19.4 | — |
|  | 4 | 1 | 19.4 | — |
|  | 5 | 1 | 12.6 | 119 |
|  | 5 | 2 | 12.6 | 43.5 |
|  | 6 | 1 | 12.6 | 216.6 |
|  | 6 | 2 | 12.6 | 240 |
|  | 8 | 1 | 12.6 | 120 |
|  | 8 | 2 | 19.4 | 85 |
|  | 9 | 1 | 26.3 | 350 |

For the testing, although the rock bolts were numbered consecutively 1, 2, 3, 4 . . . etc., some rock bolts were not tested. Hence, rock bolt number 5 not tested at the first mine site and rock bolts 3 and 7 not being tested at the second mine site. The results Table 1 above shows the amount of slippage (movement) of the rock bolt under dynamic test in-situ for a given applied load (energy applied). As can be seen from the table, some rock bolts were tested more than once.

In use, a required amount of weight is suspended from the in-situ rock bolt/anchor through the connector 100 and shaft 118, 202 set-up. The weights are raised up the shaft and retained in that raised position via a quick release mechanism. When the quick release mechanism is operated, the weights fall down the shaft and are very rapidly stopped on impact with the base retaining plate 208 and pad 209. Kinetic energy is thus transferred through the shaft and connector to the rock bolt/anchor. That energy transfer is recorded by the load cell and any movement of the rock bolt/anchor is measured by the accelerometer.

The connector allows articulation of the shaft and weights relative to the non-vertical rock bolt/anchor so that a vertically applied force is transferred to the non-vertical rock bolt/anchor in-situ in a mine roof.

The claims defining the invention are as follows:

1. A connector arranged to attach a loading device to an in situ rock bolt or anchor bolt in a rock or concrete substrate, the connector comprising:
    a body including multiple portions that are releasably connectable together by one or more integral or detachable fasteners;
    a first attachment means arranged to attach the body to the in situ rock bolt or anchor bolt, the first attachment means including an aperture arranged to removably receive a shaft portion of the rock bolt or anchor bolt;
    an adapter arranged to connect the first attachment means to the rock bolt or anchor bolt; and
    a loading device connection, wherein the loading device connection includes a second attachment means movably attached to the body and arranged to releasably attach a loading device to the body.

2. The connector according to claim 1, wherein the body includes at least one first curved surface formed by a cavity in the body, the first attachment means including at least one second curved surface, the at least one first and second curved surfaces being corresponding surfaces.

3. The connector according to claim 2, further comprising at least one third curved surface within the cavity of the body, the first attachment means including at least one fourth curved surface arranged to contact the third curved surface to allow relative movement of the loading device and the body, wherein the at least one third and fourth surfaces are corresponding surfaces.

4. The connector according to claim 2, wherein the corresponding first and second curved surfaces include complimentary part spherical surfaces.

5. The connector according to claim 3, wherein the cooperating third and fourth surfaces includes complimentary part spherical surfaces.

6. The connector according to claim 1, wherein the fasteners include at least one retaining plate or ring with holes therethrough to receive bolts.

7. The connector according to claim 6, wherein the bolts pass through the holes in each plate or ring, and nuts attached to the bolts or engagement of the bolts to threaded holes in the plates/rings, to retain the portions together.

8. The connector according to claim 1, further comprising at least one accelerometer or at least one load cell.

9. The connector according to claim 8, wherein the at least one accelerometer is housed in the connector body.

10. The connector according to claim 8, wherein the at least one load cell is provided adjacent the second attachment means.

11. The connector according to claim 1, wherein the aperture is a tapered opening in the first attachment means, the second attachment means also including a tapered opening.

12. The connector according to claim 1, further including protection means to prevent damage to an electrical connector of a load cell provided within the connector.

13. The connector according to claim 12, wherein the protection means comprises at least one metal projection adjacent the electrical connector.

14. The connector according to claim 13, wherein the at least one metal projection includes a bolt projecting above the load cell electrical connector and a tab of a washer projecting below a load cell electrical connector.

15. The connector of claim 1, further comprising a shaft adapter connected to the second attachment means, the shaft adapter being arranged to receive a shaft of the loading device.

16. A dynamic testing system for testing rock bolts and anchor bolts in situ, the system comprising:
    a loading device; and
    a connector arranged to releasably attach the loading device to an in situ rock bolt or anchor bolt, the loading device including at least one releasable weight arranged to apply an impact load through the connector to the rock bolt or anchor bolt when released, and a weight release device, the connector including a body having at least two portions releasably connectable together, a first attachment means arranged to attach the body to the in situ rock bolt or anchor bolt, and a loading device connection, wherein the loading device connection includes a second attachment means movably attached to the body and arranged to releasably attach the loading device to the body.

17. The system of claim 16, wherein the at least two portions are releasably connectable together by one or more integral or detachable fasteners.

* * * * *